United States Patent
Dreyfuss

(10) Patent No.: US 9,421,010 B2
(45) Date of Patent: Aug. 23, 2016

(54) WHIPPING SUTURE ANCHOR

(71) Applicant: Arthrex, Inc., Naples, FL (US)

(72) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 387 days.

(21) Appl. No.: 13/891,391

(22) Filed: May 10, 2013

(65) Prior Publication Data

US 2013/0345748 A1    Dec. 26, 2013

Related U.S. Application Data

(60) Provisional application No. 61/661,859, filed on Jun. 20, 2012.

(51) Int. Cl.
| | |
|---|---|
| *A61B 17/04* | (2006.01) |
| *D07B 7/16* | (2006.01) |
| *D02G 3/36* | (2006.01) |
| *D07B 1/18* | (2006.01) |

(52) U.S. Cl.
CPC .............. *A61B 17/0401* (2013.01); *D02G 3/36* (2013.01); *D07B 7/167* (2013.01); *A61B 2017/0464* (2013.01); *D07B 1/18* (2013.01); *D07B 2205/2014* (2013.01)

(58) Field of Classification Search
CPC .................. A61B 17/0401; A61B 2017/0464; D02G 3/36; D07B 7/167; D07B 1/18; D07B 2205/2014
See application file for complete search history.

(56) References Cited

U.S. PATENT DOCUMENTS

| | | | |
|---|---|---|---|
| 5,370,662 A * | 12/1994 | Stone et al. | ................... 606/232 |
| 5,989,252 A | 11/1999 | Fumex | |
| 6,296,659 B1 | 10/2001 | Foerster | |
| 6,511,498 B1 | 1/2003 | Fumex | |
| 6,716,234 B2 | 4/2004 | Grafton et al. | |
| 7,329,272 B2 | 2/2008 | Burkhart et al. | |
| 7,803,173 B2 | 9/2010 | Burkhart et al. | |
| 7,892,256 B2 | 2/2011 | Grafton et al. | |
| 8,118,836 B2 | 2/2012 | Denham et al. | |
| 2006/0089646 A1* | 4/2006 | Bonutti | .......................... 606/61 |
| 2007/0135843 A1 | 6/2007 | Burkhart | |

(Continued)

FOREIGN PATENT DOCUMENTS

| | | |
|---|---|---|
| EP | 2 277 457 A1 | 1/2011 |
| WO | WO 2007/005394 A1 | 1/2007 |
| WO | WO 2009/029914 A1 | 3/2009 |

OTHER PUBLICATIONS

R. Glousman et al., "JuggerKnot Soft Anchor." Labral Repair, Surgical Protocol, Biomet Sports Medicine, www.biometsportsmedicine.com, 2010, 2011.

*Primary Examiner* — Ashley Fishback
(74) *Attorney, Agent, or Firm* — Blank Rome LLP

(57) ABSTRACT

A fixation device for fixation of soft tissue to bone with a body formed essentially of resorbable or non-resorbable yarns. The fixation device may be a knotted or a knotless construct. The fixation device is a soft, yarn-based whipping anchor which is formed by providing a suture eyelet, and passing a plurality of passes of yarns around the suture eyelet (forming a whipping twine), using the suture eyelet as a mandrel, to create a robust construct which may have geometrically-shaped features such as barbs. The eyelet and the twine may be made from resorbable material, non-resorbable material, or combination of resorbable and non-resorbable materials.

21 Claims, 1 Drawing Sheet

(56) References Cited

U.S. PATENT DOCUMENTS

| | | |
|---|---|---|
| 2007/0185532 A1 | 8/2007 | Stone et al. |
| 2009/0306711 A1 | 12/2009 | Stone et al. |
| 2009/0318961 A1 | 12/2009 | Stone et al. |
| 2011/0098727 A1 | 4/2011 | Kaiser et al. |
| 2012/0150203 A1 | 6/2012 | Brady et al. |
| 2013/0018416 A1 | 1/2013 | Lombardo et al. |
| 2013/0110165 A1 | 5/2013 | Burkhart et al. |

* cited by examiner

WHIPPING SUTURE ANCHOR

CROSS-REFERENCE TO RELATED APPLICATIONS

This application claims the benefit of U.S. Provisional Application No. 61/661,859 filed Jun. 20, 2012, the disclosure of which is incorporated by reference in its entirety herein.

FIELD OF THE INVENTION

The present invention relates to surgical devices and, in particular, to suture anchors and methods of repairing or fixation of soft tissue to bone.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor fixed in a hole provided in the bone.

It would be desirable to provide a suture construct that is formed essentially of soft material(s) such as fibers, yarns, filaments suture or suture-based materials or other soft materials and/or compositions, with the ability to be inserted into a bone socket and provide increased strength for tissue fixation.

SUMMARY OF THE INVENTION

The present invention provides a fixation device (a soft yarn-based anchor) for fixation of soft tissue to bone which is formed essentially of resorbable or non-resorbable materials. The fixation device may be a knotted or a knotless anchor construct.

The anchor of the present invention is a whipping anchor formed by: (i) providing an eyelet; and (ii) whipping a twine or whipcord around the eyelet by using the eyelet as a mandrel, to create a robust construct which may have geometrically-shaped features such as barbs. The eyelet and the twine may be made from resorbable material, non-resorbable material, or combination of resorbable and non-resorbable materials. In additional embodiments, the mandrel may be a removable pin which could create a hollow or cannulated part after fabrication.

These and other features and advantages of the invention will be more apparent from the following detailed description that is provided in connection with the accompanying drawing and illustrated exemplary embodiments of the invention.

DETAILED DESCRIPTION OF THE EMBODIMENTS

The present invention provides surgical systems, fixation devices and methods for knotted or knotless soft tissue (ligament, tendon, graft, etc.) repair and fixation, such as fixation of soft tissue to bone. The fixation device of the present invention is a whipping anchor with a body formed of suture or similar material that forms a loop (eyelet), and at least one whipping twine surrounding the suture eyelet. The whipping twine may be in the form of a yarn, fiber, filament or suture, or combinations of these materials. Preferably, the fixation device of the present invention is a yarn-based soft anchor made up of all suture and yarn.

The present invention also provides a fixation device for fixation of soft tissue to bone which is formed essentially of resorbable or non-resorbable yarns. The fixation device may be a knotted or a knotless anchor construct.

The fixation device of the present invention is formed by: (i) providing a suture eyelet; and (ii) whipping a twine around the suture eyelet by passing a plurality of passes of the twine around the suture eyelet (forming a whipping twine) and using the suture eyelet as a mandrel, to create a robust whipping construct. The whipping construct may have geometrically-shaped features such as barbs, knots, indentations and/or protuberances, or similar structures. The eyelet and the twine may be made from resorbable material, non-resorbable material, or combination of resorbable and non-resorbable materials. The eyelet and the twine may be made of synthetic or natural materials.

As detailed below, the whipping suture anchor of the present invention is formed by yarn whipping in a manner similar to rope or cord whipping employed in boating and maritime applications, for example. The whipping can be conducted so that multiple turns of twine or whipcord (i.e., whipfilament and/or whipyarn and/or whipfiber) are tightly wrapped around the suture eyelet to prevent the two ends of the suture to become apart.

Figure 1:
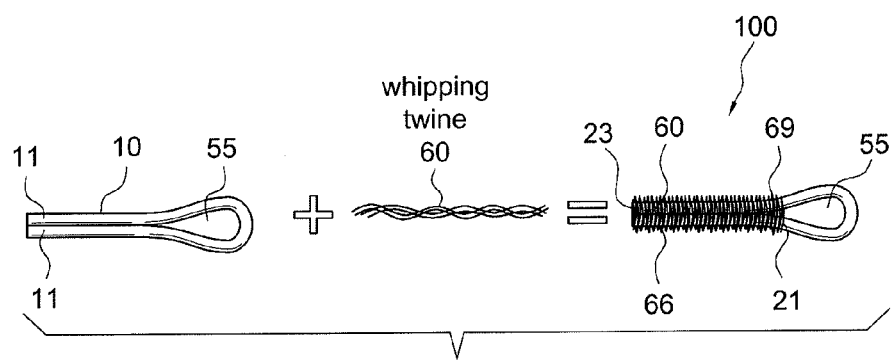
FIG. 1 illustrates steps of assembling a yarn-based anchor (whipping suture anchor) according to an exemplary embodiment of the present invention.
Figure 2:
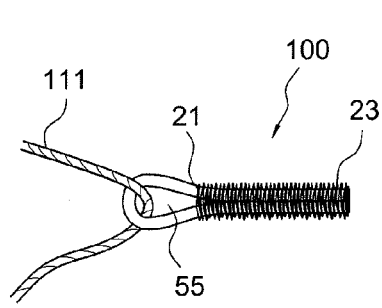
FIG. 2 illustrates the yarn-based anchor (whipping suture anchor) of FIG. 1 with tying sutures attached to the eyelet.
Figure 3:
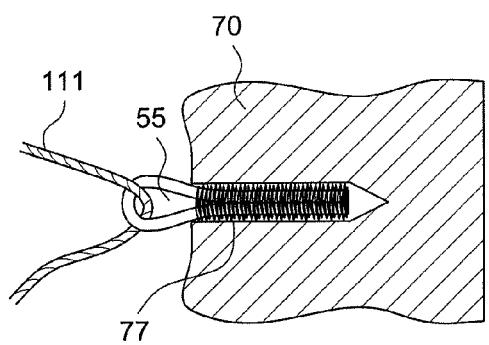
FIG. 3 illustrates the yarn-based anchor (whipping suture anchor) of FIG. 2 inserted into a bone tunnel or socket.

Referring now to the drawings, where like elements are designated by like reference numerals, FIGS. 1-3 illustrate an exemplary fixation device 100 of the present invention in the form of a yarn-based suture anchor or soft suture anchor implant. Anchor 100 includes a flexible strand 10 (for example, a suture such as a FiberWire® suture 10) that forms eyelet 55 or closed loop 55 when the two free ends 11 of suture 10 are brought together such that the free ends 11 are abutting one another, as seen in FIG. 2. Fixation device 100 also includes a whipping twine body 66 formed of at least one pass of at least one twine 60 (in the form of any resorbable or non-resorbable material such as yarn, fiber, filament, suture 60) surrounding the suture eyelet. If desired, multiple twines 60 may be employed.

Flexible strand 10 may consist essentially of suture. Flexible strand 10 may be formed of resorbable material or non-resorbable material, and of natural or synthetic materials. If desired, multiple flexible strands 10 are employed to form fixation device 100 in which case the whipping twine will surround multiple ends of all (or only part) of the multiple flexible strands 10.

Twine 60 may be any resorbable or non-resorbable material that can undergo whipping, i.e., multiple turns or passes of twine that are tightly wrapped around the two (or more) free ends of flexible strand 10.

In an exemplary embodiment, the fixation device 100 of the present invention is a whipping suture anchor formed by yarn whipping in a manner similar to rope or cord whipping employed in boating and maritime applications, for example. As detailed below, the whipping can be conducted so that multiple turns of twine or whipcord 60 (i.e., whipfilament and/or whipyarn and/or whipfiber) are tightly wrapped around the suture eyelet to prevent the two (or more) ends of the suture to become apart. Whipping may be applied by hand or by using a needle, and secured to the whipping body or to itself, to complete the formation of the fixation device.

As such, and according to an exemplary-only embodiment of the present invention, a method of assembling fixation device 100 includes the step of using suture eyelet 55 as a mandrel. A plurality of passes of at least one twine or whipcord (i.e., whipfilament and/or whipyarn and/or whipfiber) are formed around the two free ends 11 of strand 10 and abutting the suture eyelet 55 at proximal end 21 of the fixation device 100, as shown in FIG. 1, to form whipping twine body 66. The whipping is conducted so that multiple turns of at least one twine 60 are tightly wrapped around the suture eyelet 55 to prevent the two ends 11 of the suture 10 from coming apart. As seen in FIGS. 1-3, the twine 60 extends around the two ends 11 of the suture 10 and does not extend between the free ends 11 (which abut one another). According to an exemplary-only embodiment, the whipping is conducted so that multiple turns/passes extend along the whole length of the free ends 11, i.e., extending from proximal end 21 to distal end 23, as shown in FIGS. 1 and 2. The whipping may be also conducted, however, only along some of the regions of the free ends 11, for example, only at the proximal end 21 and at the distal end 23.

Whipping may be applied by hand or by using a needle. Either way, and subsequently to the whipping, the twine is either tied off and the ends of the twine are secured into or behind the whipping, or the ends of the twine are sewed (stitched) to adjacent strands or through the twine (yarn) itself, to complete the formation of the fixation device. Whipping anchor 100 may be provided with geometrically-shaped features 69 (FIG. 1) such as barbs, knots or similar structures.

An exemplary method of forming soft, yarn-based whipping anchor 100 according to the present invention comprises the steps of: (i) providing a suture eyelet 55 of a suture strand 10 by bringing together the two free ends 11 of the strand 10; and (ii) forming a plurality of turns/passes of at least one twine 60 (yarn/fiber/suture/filament 60) around the free ends 11 of the strand 10 and along a length of the free ends 11 (using the suture eyelet 55 as a mandrel) to form a whipping twine body 66 adjacent the suture eyelet 55. Whipping twine body 66 surrounds the two free ends 11. In additional embodiments, the mandrel may be a removable pin which could create a hollow or cannulated part after fabrication.

In additional embodiments, the whipping may be conducted only around certain regions/portions of the length of the free ends 11, i.e., not throughout the whole length as shown in FIGS. 1 and 2. For example, a first whipping with a first twine may be conducted adjacent the eyelet 55 and proximal end 21, and a second whipping with a second twine (which may be formed of a material similar to or different from that of the first twine) may be conducted adjacent the distal end 23.

FIG. 3 illustrates insertion and fixation of exemplary fixation device 100 of the present invention into bone socket/tunnel/hole 77 formed within bone 70. At least one tying suture 111 is attached to tissue (for example, soft tissue to be repaired). Additional arthroscopic sutures (such as tying or sliding sutures) attached to tissue (such as soft tissue) may be threaded through the eyelet 55 of the soft suture anchor 100 to allow secure fixation of the tissue to bone, as desired and depending on the specific characteristics of each surgical repair. The separate eyelet component 55 provides resistance to cut-through during sliding knot techniques and improved tissue fixation relative to the yarn-based body.

The eyelet 55 and the twine 60 may be made from resorbable material, non-resorbable material, or combination of resorbable and non-resorbable materials. The eyelet 55 and the twine 60 may be formed of natural or synthetic materials, or combinations of these materials. The twine 60 may be formed of yarns, fibers, filaments, sutures, suture-based materials, or similar soft materials that allow whipping and formation of a whipping twine body such as body 66 described above. Preferably, the whipping twine 60 consists essentially of yarns.

The at least one twine may be braided, knitted or woven and may be formed of a same material or combination of different materials (i.e., different yarns/fibers/sutures/filaments of different materials).

The at least one twine may be absorbable, resorbable, partially resorbable or non-resorbable. Preferably, the at least one twine may include at least one biomedical grade resorbable polymer such as PGA, PLLA and their copolymers (i.e., copolymers of glycol and lactic acid), and also others such as PDO, PHA, p(G-TMC), PCL, among others.

The at least one twine may contain at least one long continuous length of interlocked fibers, such as threads or textile yarns or filaments. The yarns may be also formed of polypropylene yarn with a deposited layer of cross-linked beef-originated collagen. The yarns may further be partially or totally resorbable (for example, manufactured of resorbable polyglactine) and/or nonresorbable (for example, nonresorbable polypropylene threads).

In additional embodiments, the at least one twine may further include spongy biological material(s) which may contain interstitial spaces and channels that allow cellular invasion and growth (for example, fibroblast proliferation to allow tissue regeneration). The spongy biological material(s) may optionally comprise additional components such as blood, proteins, growth factors or chemicals that may be provided (by injection or impregnation, for example) within the material(s).

As such, and in accordance with exemplary-only embodiments, the at least one whipping twine 60 may be employed to deliver to the surgical site (bone tunnel or socket) a biological component which includes at least one of blood, blood components or fractions, PRP, bone marrow aspirate (BMA) or autologous conditioned plasma (ACP). The biological component may be provided (by injection, impregnation or soaking, for example) directly into the whipping twine 60 and prior to or after the whipping step, but before the insertion of the anchor into the site or into the anatomical tissue. In yet another embodiment, the anchor is first inserted into the repair site and then the whipping twine body 66 is injected with the biological component (for example, PRP, BMA or ACP). If desired, whipping twine 60 may be fabricated to additionally comprise components such as growth factors, additional antiseptic chemicals and/or antibiotics and/or electrolytes, or hormones or site-specific hybrid proteins (that promote or enhance the wound healing effectiveness of the growth factors), or glue such as fibrin glue and/or adhesives, among others.

If retention of the biological components by the whipping twine 60 is desired, at least a portion of the outer surface of the whipping twine 60 and/or of the whipping twine body 66 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings.

In an exemplary embodiment only, the whipping twine 60 is a member having a generally overall cylindrical configuration and consisting essentially of yarns, and the flexible strand 10 is formed of FiberWire® suture (disclosed in U.S.

Pat. No. 6,716,234, the disclosure of which is incorporated herein by reference in its entirety). If desired, the flexible strand 10 may be provided with optional colored strands to assist surgeons in distinguishing between suture lengths. Preferably, the suture eyelet 55 and the suture strand 10 of the whipping suture anchor 100 are formed essentially of suture, for example, FiberWire® suture. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material. The preferred FiberWire® suture includes a core within a hollow braided construct, the core being a twisted yarn of UHMWPE.

Alternatively, the suture strand 10 of the suture anchor 100 may be formed of TigerWire® suture, or suture chain (such as FiberChain® disclosed in U.S. Pat. No. 7,803,173) or suture tape (such as FiberTape® disclosed in U.S. Pat. No. 7,892,256), or nitinol, among others, or combination of these materials.

If suture tape is employed for the formation of suture anchor 100, the suture tape may be a FiberTape® as disclosed in U.S. Pat. No. 7,892,256, the disclosure of which is herein incorporated by reference. The suture tape may have the same, uniform width or may have different widths, and may comprise the same or different materials.

If a chain or suture chain is employed for the formation of anchor 100, the suture chain that may be used in the present application is described in U.S. Pat. No. 7,803,173 and/or in U.S. Patent Appl. Publ. No. 2007/0135843, the disclosures of both of which are incorporated by reference in their entirety herewith.

The flexible material 10 forming the suture anchor 100 may be also formed of suture tape or a combination of suture and tape, a stiff material, or combination of stiff and flexible materials, depending on the intended application.

The whipping suture anchor 100 of the present invention may be employed for attachment of tissue (for example, soft tissue) to bone or other tissue. Additional sutures (such as sliding sutures or tying sutures 111) attached to tissue (such as soft tissue) may be threaded through the eyelet 55 of the whipping suture anchor 100, to allow secure fixation of the tissue to bone, as desired and depending on the specific characteristics of each surgical repair.

Fixation device 100 (soft anchor implant 100 or whipping anchor 100) may be employed for exemplary tissue repairs, for example, soft tissue repairs such as PASTA repairs (Partial Articular-Sided Tendon Avulsion repairs). The yarn-based soft anchors of the present invention (such as anchor 100 detailed above) are smaller than the conventional bone anchors (which are relatively large) and are formed of a soft material (resorbable or non-resorbable yarns) in contrast to the conventional anchors which are typically formed of hard materials such as PEEK, PLLA, bTCP, metal, PGA, biomaterials, etc. The soft anchor implants may be employed in percutaneous insertions by simple surgical techniques, with multiple additional indications, to provide biomechanically strong constructs.

The soft suture anchors of the present invention have applicability to repair applications that may be employed in surgical procedures such as rotator cuff repair, Achilles tendon repair, patellar tendon repair, ACL/PCL reconstruction, hip and shoulder reconstruction procedures, and any application used with fixation devices including at least one suture anchor.

The soft anchors detailed above may be also employed in conjunction with additional various knotted and/or knotless fixation devices (or combination of such knotted and knotless fixation devices), such as PushLock® anchors and/or SwivLock® anchors to secure, for example, a medial row on rotator cuff repairs.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed is:

1. A suture anchor consisting essentially of:
 a material strand with two ends abutting one another to form a free ends region and an eyelet;
 multiple twine passes provided along and around the free ends region and adjacent the eyelet of the material strand, wherein the multiple twine passes are formed by whipping at least one twine around the material strand to prevent the two ends of the material strand to become apart; and
 at least another flexible strand threaded through the eyelet for further securement of soft tissue to bone.

2. The suture anchor of claim 1, wherein the multiple twine passes are formed essentially of resorbable or non-resorbable material.

3. The suture anchor of claim 1, wherein the at least one twine is a yarn, a filament, a fiber strand, or a suture strand.

4. The suture anchor of claim 1, wherein the eyelet is formed at a most proximal end of the suture anchor.

5. The suture anchor of claim 1, wherein the material strand is one of a suture strand, a nitinol strand, a suture tape, a collagen tape or a suture chain.

6. The suture anchor of claim 1, wherein the material strand is a suture formed of ultrahigh molecular weight polyethylene.

7. The suture anchor of claim 1, wherein the suture anchor is formed by the steps of folding the material strand to form the eyelet and the free ends region; and
 conducting a plurality of passes of at least one yarn around the free ends region and adjacent the eyelet, while the eyelet acts as a mandrel, to form the suture anchor.

8. A suture anchor for surgical repairs consisting essentially of:
 a body formed of at least one whipping twine in the form of resorbable yarns;
 a flexible strand extending through the body, wherein the flexible strand has two free ends that form a closed eyelet located at one end of the body and the at least one whipping twine extends around the two free ends and not between the two free ends; and
 at least one tying or sliding suture threaded through the closed eyelet for further securement of soft tissue to bone.

9. The suture anchor of claim 8, wherein the whipping twine is one of a yarn, a filament, a fiber strand or a suture strand.

10. The suture anchor of claim 8, wherein the body consists essentially of yarns and the flexible strand is a high strength suture.

11. The suture anchor of claim 8, wherein the flexible strand is a suture strand, nitinol strand, a suture tape or a suture chain.

12. The suture anchor of claim 8, wherein the whipping twine further comprises a biological component selected from the group consisting of platelet-rich plasma, autologous conditioned plasma and bone marrow aspirate.

13. The suture anchor of claim 8, wherein the two free ends of the flexible strand abut one another.

14. A method of fixation of a first tissue to a second tissue, comprising the steps of:
providing a suture anchor comprising a length of a flexible strand folded to form a closed eyelet and a free ends region and at least one body member formed at least partially around and at least partially along the length of the flexible strand and around two ends of the free ends region without extending between the two ends of the free ends region and adjacent to the closed eyelet, the closed eyelet being located at a most proximal end of the suture anchor, the body member consisting essentially of yarns;
threading suture through the closed eyelet;
placing the suture anchor into bone; and
securing soft tissue to bone with the suture.

15. The method of claim 14, wherein the suture anchor is installed into a bone tunnel or socket.

16. The method of claim 14, wherein the flexible strand is one of a suture strand, a suture tape, a suture chain or a nitinol strand.

17. The method of claim 14, further comprising the step of bringing together the two ends of the free ends region such that the two ends abut one another.

18. A method of forming a suture anchor, comprising the steps of:
bringing together two free ends of a flexible strand so that the two free ends abut one another and form a free ends region and an eyelet adjacent the free ends region; and
using the eyelet as a mandrel, conducting a plurality of passes with at least one twine around the free ends region and along a length of the free ends region and adjacent the eyelet, to form a whipping twine body abutting the eyelet, the plurality of passes preventing the two free ends of the flexible strand from becoming apart.

19. The method of claim 18, wherein the twine is a yarn, a filament, a fiber strand or a suture strand.

20. The method of claim 18, further comprising the step of providing a biological material to the twine.

21. The method of claim 20, wherein the biological material is selected from the group consisting of blood, blood components, bone marrow aspirate, platelet rich plasma, autologous conditioned plasma, proteins, growth factors and hormones.

* * * * *